United States Patent [19]
Wess et al.

[11] Patent Number: 4,805,600
[45] Date of Patent: Feb. 21, 1989

[54] COUPLING THE BODY OF A PATIENT TO A MEMBRANE

[75] Inventors: Othmar Wess, Munich; Reiner Groezinger, Alling; Kai Isdebski, Saulgau; Manfred Windsheimer, Germering; Wolfgang Erhardt, Fuerstenfeldbruck, all of Fed. Rep. of Germany

[73] Assignee: Dornier Medizintechnik GmbH, Friedrichshafen, Fed. Rep. of Germany

[21] Appl. No.: 942,252

[22] Filed: Dec. 16, 1986

[30] Foreign Application Priority Data

Dec. 18, 1985 [DE] Fed. Rep. of Germany ....... 3544710

[51] Int. Cl.$^4$ ............................................. A61H 1/00
[52] U.S. Cl. ................................... 128/24 A; 128/803
[58] Field of Search ................... 73/644; 128/639–641, 128/660, 24 A, 328, 783, 798, 802, 803

[56] References Cited

U.S. PATENT DOCUMENTS

| | | | |
|---|---|---|---|
| 3,340,868 | 9/1967 | Darling | 128/640 |
| 3,631,714 | 1/1972 | Cressman | 73/644 |
| 3,702,613 | 11/1972 | Panico et al. | 128/803 |
| 4,166,457 | 9/1979 | Jacobsen et al. | 128/639 |
| 4,464,412 | 8/1984 | Washburn | 128/803 |
| 4,700,710 | 10/1987 | Hoffman | 128/798 |

FOREIGN PATENT DOCUMENTS

0724144  3/1980  U.S.S.R. .............................. 128/803

*Primary Examiner*—Ruth S. Smith
*Attorney, Agent, or Firm*—Ralf H. Siegemund

[57] ABSTRACT

The body of a patient is gaplessly coupled to the membrane of therapeutic equipment through a gel layer; a gel releasing bag is placed upon the membrane and the membrane is moved towards the body; subsequently, the bag is removed from the gap that forms between the skin of the patient and the membrane whereby gel emerges from one or several openings, filling the gap completely with gel as the bag is squeezed and removed.

3 Claims, 1 Drawing Sheet

COUPLING THE BODY OF A PATIENT TO A MEMBRANE

BACKGROUND OF THE INVENTION

The present invention relates to a method and equipment for coupling a membrane to the skin of a human being, and particularly the invention relates to coupling equipment to a human being for purposes of transmission of shock waves or the like.

Medical diagnoses and therapy using particular equipment, often requires that, in a mechanical sense, that equipment is to be coupled to the body of the patient. Specifically, a transmission path is to be established between the body of the human being/patient and the equipment. This transmission may involve, for example, radiation, or mechanical waves, to be transmitted from the equipment into the body of the patient, without incurring losses generally, and without unduly and unforeseeably varying the transmission path of these waves or radiation. Equipment of the type to which the invention pertains relates, for example, to lithotripsy, but can be used in other equipment as well.

In preparation of coupling such equipment to the body of a human being, it is customary to remove body hair from the skin, so as to avoid immediate and direct interference by the hair of the skin upon the equipment and the coupling to be effected. In addition, a certain gel or pasty material is placed upon the skin of the body such that any physical equipment, such as a membrane, an electrode, or the like, will, in fact, uniformly contact this particular coupling material. On the other hand, this coupling material gaplessly abuts and adheres to the body and the skin of the patient. This paste, in other words, has as its primary function, the removal of any transmission path uncertainty between equipment, on one hand, and the skin of the human being, on the other hand. One is no longer dependent upon a clearly uniform gapless abutment of equipment itself and the skin of the patient. The interpositioning of a paste removes so to speak any inherent irregularity that may present itself, if an immediate and direct "dry" contact were effected.

A problem has been observed in a sense that upon applying this paste to the skin of the human patient and then attaching the equipment to that paste, there still is the possibility that air bubbles get trapped, and, therefore, provide for a certain local non-uniformity. Clearly, medical technical personnel or physicians may acquire personal skills sufficient to avoid irregularities on that account, and particularly they may well be aware of the strict avoidance of any manipulation that may result in the inclusion of such air bubbles. On the other hand, it is immediately apparent that the avoidance of the inclusion of air bubbles in the transmission path between equipment and the patient does become a matter of personal skill but also personal, i.e., subjective judgment. This may well be satisfactory in many instances but it is obvious on its face that it is easy to conceive instances in which this kind of a reliance is no longer justified.

It has, therefore, been suggested to provide, as an additional step for an evacuation procedure of any space between the skin of the patient on one hand, and a membrane for coupling, on the other hand. While basically satisfactory and particularly satisfactory in principle, it simply was found as a matter of practice that isolated air bubbles still remain trapped "somehow".

In the field of contactless lithtropsy, i.e. the contactless comminution of concrements in the body of a human being, the foregoing problem has been avoided in the past entirely by simply placing the patient into a tub filled with water, and there is an immediate and interface free transmission path provided between the liquid as it flushes around the body of the patient, on one hand, and a source of shock waves, on the other hand. The source of shock waves is simply in immediate and direct contact with that coupling fluid, so that there is no danger of interference on account of any physical, mechanical interface within the system and providing some kind of barrier between the shock wave generation and the skin of the patent, on the other hand. However, the utilization of such a tub is not too satisfactory.

DESCRIPTION OF THE INVENTION

It is an object of the present invention to provide a new and improved method and equipment by means of which it can be made sure that even less trained personnel handling the equipment can reliably be made sure to establish an air gap free contact and engagement of a membrane closing off a shock wave generating equipment and the skin of the patient.

It is a specific object of the present invention to improve coupling of shock wave generators to the body of a patient without requiring a water filled tub.

In accordance with the preferred embodiment of the present invention, it is suggested to provide between the surface (skin) of the body of a patient and a membrane, a gel releasing, flexible container such as a bag, a hose, a pouch or the like, which bag is removed from the gap between the equipment and the patient prior to the completion of immediate and intimate contact between the equipment and the patient and wherein the gel emerges, under excess pressure, from one of several openings in that bag and fills the aforementioned gap completely and without the inclusion of air bubbles. In furtherance of the invention, the skin part of the patient is covered with a gel initially as the patient is assumed to rest on a suitable support. Subsequently, a gel filled flat container is placed on the patient and the equipment, such as a shock wave generator of the type referred to above is moved towards the body of the patient. Thereafter the bag is removed while air bubbles are stripped off and gel emerges from the bag along some edge thereof. Further release of gel is then provided by an additional bag squeezing operation.

DESCRIPTION OF THE DRAWINGS

While the specification concludes with claims particularly pointing out and distinctly claiming the subject matter which is regarded as the invention, it is believed that the invention, the objects and features of the invention, and further objects, features, and advantages thereof will be better understood from the following description taken in connection with the accompanying drawings in which:

Proceeding now to the detailed description of the drawings, FIG. 1 illustrates basically a rectangular bag or pouch 2 made of synthetic foil material. The bag 2 contains a gel 4 and has a front edge to which is welded a rod 6. The rod 6 is provided with a plurality of bores 8, openings, or slots after a protective foil 10 has been removed from this rod, gel 4 may emerge. This emergence and extraction is particularly provided by operation of a squeezing device 12, shown in FIG. 1, and including two squeezing drums or rolls 14 and 16, a frame 20, and a crank 22.

In FIG. 2 the gel bag 2 and the rod 6 are shown in section. An opening 8 is readily revealed in the enlargement of FIG. 3. FIGS. 2 and 3, moreover, show the rod 6 to be an additional element. On the under shows the rod 6 as an additional element. On the under side, as well as the upper side of the rod are strippers 24. These strippers 24 serve to remove air bubbles from the previously applied gel. The openings 8 are constructed for minimum resistance as to any flow of the pasty substance.

FIG. 4 illustrates bellows 26 mounted in a frame 28, and a membrane 30 establishes therewith a closed water filled space. On the other end of that space, a treatment device, for example, the shock wave generator coupled to the membrane 30. The body 32 of the patient has been prepared by covering the portions of the skin where coupling is provided with a gel. The patient wil be placed in a position by means of a rest (not shown) which position is dictated by the thereby and the details of the treatment equipment. The inventive bag 2 has been placed upon membrane 30.

Figure 1:
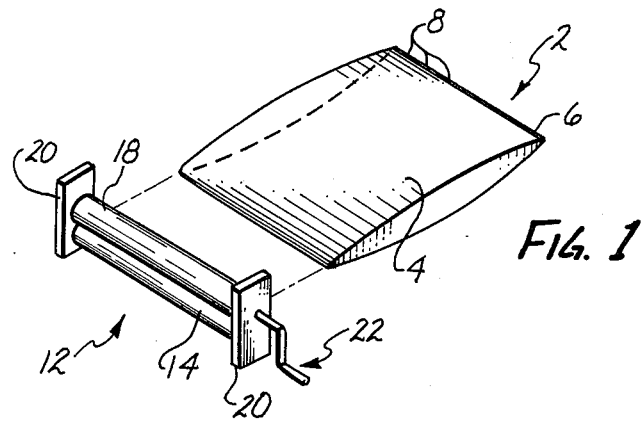
FIG. 1 illustrates equipment for practicing the invention, including a gel filled bag in accordance with the preferred embodiment of the present invention for practicing the best mode thereof.
Figure 2:
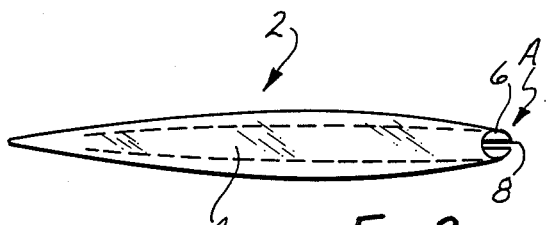
FIG. 2 illustrates a cross-section through that gel bag, shown in FIG. 1.
Figure 3:
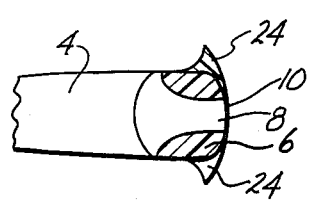
FIG. 3 illustrates an enlarged detail indicating by the letter A in FIG. 2.
Figure 4:
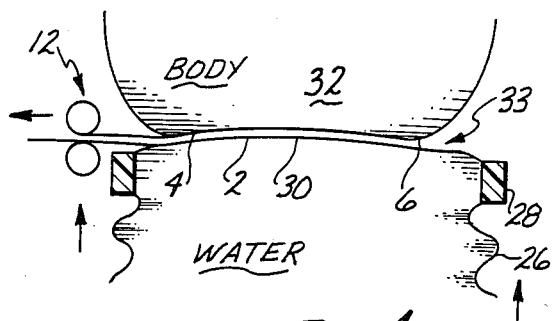
FIG. 4 is an illustration of the basic mode of operation and function of the equipment in accordance with the present invention and as depicted in FIGS. 1, 2, and 3.

As soon as the bellows 26 move in direction of the arrow, and as soon, therefore, as a narrow gap 33 develops between the member 32 and the membrane 30, under inclusion of the bag 2 being interposed, one will remove the bag 2 by means of the squeezing device 12. Thereafter, the gap 33 is filled with gel 4. This way, one obtains an air gapless coupling of body 32 to the membrane 30 of the treatment equipment.

Figure 5:
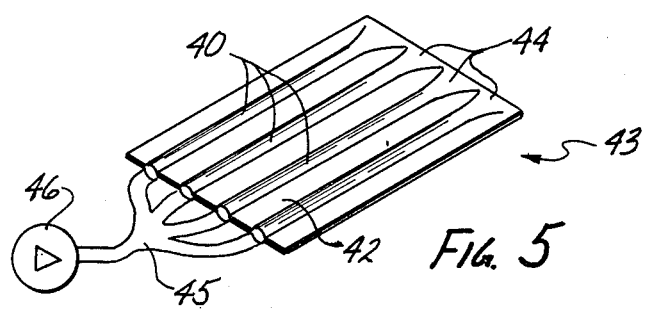
FIG. 5 illustrates a modified embodiment relying basically on the embodiment shown in FIG. 1, but showing additional features that are useful in certain instances.

FIG. 5 illustrates another embodiment of the invention. Here are shown several hoses 40 to be welded into a foil 42. The openings 44 of the hoses are configured such that they occupy almost the entire front face of that foil. The hoses 40 are connected to a manifold or connecting line 45, and are provided with gel by means of a pump 46. Also, in this case, one of several strippers may be provided at the opening 44.

The invention is not limited to the embodiments described above, but all changes and modifications thereof, not constituting departures from the spirit and scope of the invention are intended to be included.

We claim:

1. Method for air gaplessly coupling the body of a human being to the membrane of therapeutic shock wave equipment by providing on the body a gel layer through which shock waves are to be transmitted without attentuation, comprising:
    placing a gel releasing bag upon said membrane, the bag having at least one opening along one edge of the bag;
    moving the membrane towards said body; and
    removing said bag from the gap between the skin of the patient and the membrane whereby a gel layer emerges from said at least one opening along the one edge and fills the gap completely with gel as the bag is removed.

2. The method as in claim 1, and including squeezing the bag upon removing the bag from the gap between the body and the membrane.

3. The method as in claim 1 including the step of squeezing gel in multiple stream from multiple openings in the bag as the bag is removed.

* * * * *